US006435873B1

(12) United States Patent
Burgio

(10) Patent No.: US 6,435,873 B1
(45) Date of Patent: Aug. 20, 2002

(54) MEDICATION DELIVERY DEVICES

(75) Inventor: Paul A. Burgio, Grant, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/685,177

(22) Filed: Oct. 10, 2000

(51) Int. Cl.[7] ................................................. A61K 6/02
(52) U.S. Cl. ........................ 433/80; 433/215; 424/401
(58) Field of Search .......................... 433/80, 215, 216; 424/401, 49, 53

(56) References Cited

U.S. PATENT DOCUMENTS

| | | | |
|---|---|---|---|
| 3,972,995 A | 8/1976 | Tsuk et al. ..................... | 424/28 |
| 4,290,174 A | 9/1981 | Kalleberg ..................... | 24/204 |
| 4,619,979 A | 10/1986 | Kotnour et al. ................ | 526/88 |
| 4,843,134 A | 6/1989 | Kotnour et al. .......... | 526/318.4 |
| 4,984,339 A | 1/1991 | Provost et al. ................ | 24/452 |
| 5,152,917 A | 10/1992 | Pieper et al. ................. | 51/295 |
| 5,344,681 A | 9/1994 | Calhoun et al. .............. | 428/42 |
| 5,449,540 A | 9/1995 | Calhoun et al. .............. | 428/42 |
| 5,500,273 A | 3/1996 | Holmes et al. ............. | 428/147 |
| 5,637,646 A | 6/1997 | Ellis ........................... | 525/309 |
| 5,670,557 A | 9/1997 | Dietz et al. ................. | 522/184 |
| 5,674,561 A | 10/1997 | Dietz et al. ............... | 427/208.4 |
| 5,804,610 A | 9/1998 | Hamer et al. ................ | 522/182 |
| 5,879,691 A | 3/1999 | Sagel et al. .................. | 429/401 |
| 5,891,453 A | 4/1999 | Sagel et al. .................. | 424/401 |
| 5,894,017 A | 4/1999 | Sagel et al. .................. | 424/401 |
| 5,989,569 A | 11/1999 | Dirksing et al. ............. | 424/401 |
| 6,045,811 A | 4/2000 | Dirksing et al. ............. | 424/401 |

FOREIGN PATENT DOCUMENTS

| | | |
|---|---|---|
| EP | 0 398 229 A2 | 11/1990 |
| WO | WO94/23610 | 10/1994 |
| WO | WO98/30381 | 7/1998 |
| WO | WO98/57564 | 12/1998 |
| WO | WO99/62472 | 12/1999 |
| WO | WO00/09036 | 2/2000 |
| WO | WO00/44403 | 8/2000 |

Primary Examiner—Cary E. O'Connor

(57) ABSTRACT

A device for delivering medicaments to oral structures contains a flexible backing having a plurality of microstructures protruding from one surface of the backing, and a binder layer containing medicaments disposed on the backing and/or microstructures. Because the device contains microstructures that form obstacles or barrier that minimize the flow of medicaments away from the target oral structure, the medicaments stay at the desired longer thereby being more effective at treating the oral structure. One particularly useful application of the inventive device is for whitening teeth.

20 Claims, 1 Drawing Sheet

MEDICATION DELIVERY DEVICES

FIELD OF INVENTION

This invention pertains to devices useful for delivering medicaments to oral structures for a prolonged time. In particular, the device has a binder containing medicaments, the binder having adhesive properties and being disposed on a backing containing a plurality of microstructures.

BACKGROUND

Many methods are available to deliver medication or actives to a dental patient's teeth and/or the gum tissues (i.e., gingiva). One method involves applying medication directly to teeth surface by use of a brush or swab. This method provides advantages such as relatively low expense and can be done by the patient. It has a major disadvantage, however, because the medication typically does not remain on the oral structures for a significant length of time. The medication contact time varies and may depend on factors such as the medication viscosity and the presence of saliva. Medication effectiveness can be reduced when it is removed prematurely from the oral structure intended for treatment.

Another method uses a delivery system containing a strip of material having medicaments, typically a tooth whitening substance, applied to the strip. In use, a user places the delivery system on teeth surface such that the whitening substance contacts the teeth surface. The substance can provide adhesive attachment between the strip of material and the teeth surface to hold the delivery system in place. Such delivery systems are disclosed in U.S. Pat. No. 5,879,691 (Sagel et al.); U.S. Pat. No. 5,891,453 (Sagel et al.); 5,894,017 (Sagel et al.); 5,989,569 (Dirksing et al.); 6,045,811 (Dirksing et al.); and WO 99/62472.

Yet another method involves placing a dental tray over the dental arch. The tray usually contains a channel that receives all or at least a portion of the teeth and optionally the gingiva. In some methods, the trays are custom-made to improve the fit to the patient's dental arch. Such trays require preparation time but represent a significant improvement over mass-produced trays. The custom-made trays can be made by taking an alginate impression of the patient's oral structure and then making a model from the impression. The trays may contain reservoirs for holding the medicaments. The trays may contain support members useful for resisting the flow of medication from the reservoir in at least one of a mesial-distal direction and a gingival direction. In this way, the dental tray maintains a high concentration of the medicaments to the desired oral structure for an extended period of time. Such dental trays are disclosed in publications WO 00/09036 and WO 00/44403.

While the various technologies discussed thus far provide useful methods for delivering medicaments to desired oral structures, other devices are sought.

SUMMARY

The present invention provides a new device, typically in the form of a strip, capable of maintaining prolonged delivery of medicaments to oral structures, such as teeth and gums. As used herein, "prolonged delivery" means that the binder and/or medicaments remain near the oral structure on the order of hours. Advantageously, the inventive device does not rely on the use of a dental tray and can be applied directly on the oral structure targeted for treatment.

In one aspect, the invention provides for a device delivering medicaments for treating oral structures, the device comprising or consisting essentially of (a) a flexible backing having a first surface containing a plurality of microstructures; and (b) a binder containing medicaments disposed on at least a portion of said first surface and/or at least a portion of said microstructures. In one embodiment, the binder is tacky so as to be able to bond adhesively to the target oral structures. In another aspect, the invention provides a kit containing the device and instructions for using it. As used herein, "oral structure" means structures of or relating to the mouth, including teeth and soft tissues.

The invention also provides for various methods of delivering medicaments for treating oral structures. One illustrative method comprises or consists essentially of the following acts: (a) providing a flexible backing having a first and second surfaces, the first surface comprising a plurality of microstructures; (b) applying a binder containing medicaments to at least a portion of said first surface of the backing and/or to at least a portion of the microstructures to yield a precoated strip; then (c) applying the strip to oral structures such that the binder is proximal to the structures and the second surface of the backing lies near the buccal side. When binder lies in direct contact with the oral structure, the binder is tacky so that it can adhesively bond thereto. In an alternative method, the binder containing medicaments is first applied to the oral structures and a backing comprising microstructure elements is applied to the binder.

An advantage of the present invention is the use of microstructures on the backing. Without intending to be bound by theory, it is currently believed that the binder becomes interlocked with the microstructures. The microstructures, by virtue of their size, shape, and location, create barriers or obstacles to reduce the flow of the medicaments away from the target oral structure. The microstructures when disposed on the backing, also functions as a non-compressible space thereby allowing the medicament to be retained against the target oral structure. In this way, the oral structures are exposed to the medicaments for a longer period of time than compared to devices that do not use microstructures. This advantage translates in a reduction in the number of times a dental patient needs to change the device.

Another advantage of the present invention is that all the components can be formulated to be biodegradable, e.g., compatible with the user's digestive system. This advantage could possibly lead to improved patient compliance to treatment. This advantage would be particularly useful for tooth bleaching applications.

Yet another advantage of the present invention is the ease of use to the consumer. The inventive product has been constructed so that it can be easily removed from a carrier and placed directly on the target oral structures without the need of using other dental devices, such as dental trays. It has also been constructed with various tabs to allow medicament delivery to the buccal and the lingual tooth surfaces. It is flexible and can be trimmed as necessary to fit the user's mouth.

BRIEF DESCRIPTION OF THE DRAWINGS

The invention will be further described with reference to the drawing wherein.

DETAILED DESCRIPTION

Figure 1:
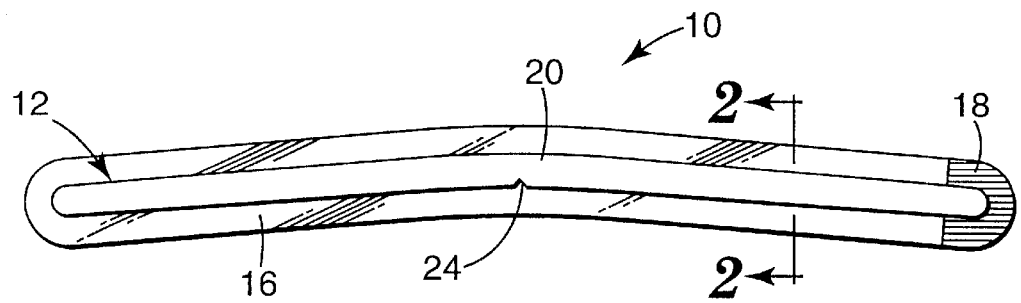
FIG. 1 is a perspective view of one illustrative embodiment of the invention.

FIG. 1 shows an assembly 10 having a device 12 for delivering medicaments (not shown) disposed on a carrier 16 and optionally a tab portion 18. The device contains a flexible backing member 20 and optionally a notch 24 on the gingival side for easy alignment of the device to the patient's oral structures. As shown, the device 12 preferably has rounded edges, i.e., no sharp edges or angles, so as to provide a comfortable fit for the user. The tab portion 18 can be of any shape and functions mainly to aid the user to remove the device 12 from the carrier 16.

Figure 2:
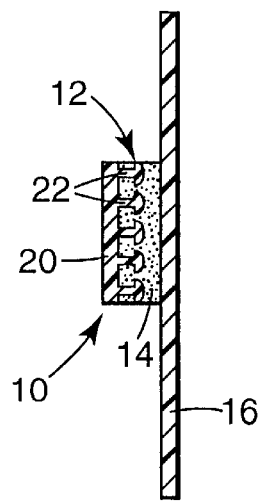
FIG. 2 is a cross-sectional view taken along line 2—2 of FIG. 1.

As shown in FIG. 2, the assembly 10 contains a carrier 16. The carrier protects the device 12 and the binder 14 during storage. The carrier also allows for ease of application by the user, who simply peels the device 12 from the carrier and apply the device directly to the user's oral structures, such as teeth. A silicone coated polyester, such as polyethylene terephthalate film, is one illustrative useful carrier. If such a carrier is used, one skilled in the art will take care so as not to use too much silicone or other materials capable of functioning as a release layer, which may affect the adhesion between the device 12 and the oral structure. The carrier preferably, but not necessarily, extends across and past the binder layer 14.

FIG. 2 further shows that the device 12 has a flexible backing member 20. Microstructures 22, shown to be integrally connected to the backing member, are disposed on a first surface of the backing 20. The binder layer 14 is disposed on at least a portion of the first surface of the backing 20 and on the microstructures 22. The total thickness of the device 12 is generally less than 5 mm, preferably less than 1 mm. Preferably, the device 12, with binder applied, is of minimal thickness so as not to feel bulky or obtrusive in the user's mouth.

Figure 3:
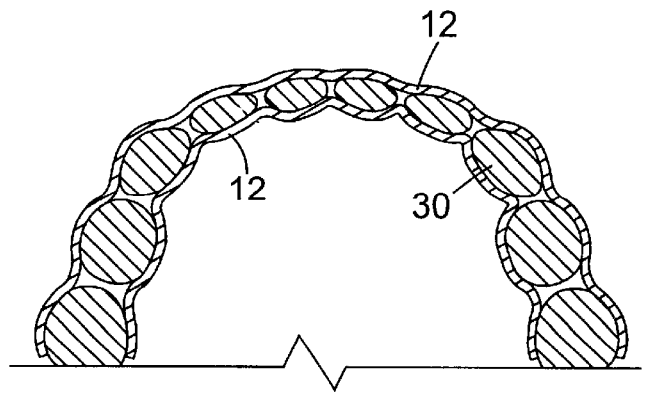
FIG. 3 is a cross-sectional view showing adjacent teeth having the inventive device attached thereto.

FIG. 3 shows the device 12 attached to a portion of the dental patient's teeth. As shown, the device can be attached to the buccal side, treating the front portion of the teeth and the lingual side, treating the back portion of the teeth. For such treatment, the device 12 can contain a tab that connects the buccal and lingual side. In use, the tab would cover a portion of the biting surface of the patient's teeth.

As shown in FIG. 2, the device 12 includes a backing 20 and a plurality of microstructures 22. In one embodiment, the microstructures are integrally connected to the backing 20. By "integrally connected," it is meant that the microstructures are formed at the same time the backing is formed. In another embodiment, the microstructures and the backing are formed separately.

U.S. Pat. No. 5,152,917 (Piper et al.) discloses one method of making the flexible backing of the inventive device. In brief summary, the method disclosed therein can be adapted for this invention as follows: (a) introducing a precursor binder into cavities contained on an outer surface of a production tool to fill such cavities; (b) introducing a backing to the outer surface of the production tool over the filled cavities such that the binder wets one major surface of the backing to form an intermediate article; (c) curing the precursor binder before the intermediate article departs from the outer surface of the production to form a flexible backing; and (d) removing the backing from the surface of the production tool. In an alternative method, the precursor binder is applied to the backing and then introduced to the production tool with the precursor binder in contact with the outer surface of the tool thereby filling the cavities. After the flexible backing is supplied by the foregoing methods, a dental binder containing medicaments can be applied, e.g., coated, on the flexible backing containing microstructures thereon.

In another embodiment, the microstructures are formed and attached, e.g., bonded, to the backing using various methods described in U.S. Pat. No. 5,500,273 (Holmes et al.). In one method, a precursor binder is fed to a production tool, which is in the form of an endless belt. The production tool, in general, contains a plurality of cavities in some desired shape, such as pyramids. The precursor binder fills at least a portion of the cavities. The precursor binder then travels through a curing zone where it is exposed to an energy source to at least partially cure the precursor binder to form solidified binder. The solidified binder is released from the production tool and further processed so as to produce a plurality of separate microstructures. The microstructures are removed from the production tool and collected in a container. The microstructures can be mixed with a dental binder containing medicaments and then coated on a flexible backing. Under this method, the microstructures are typically randomly dispersed throughout the dental binder. Alternatively the microstructures are bonded to a first surface of the flexible backing. Subsequently, a binder layer is coated thereon.

The backing member 20 can be made of various materials so long as it is flexible, compatible with the binder, medicaments, and the user, and easily conforms to the oral structure. Suitable backing members include polymers, synthetic and natural wovens, non-wovens, foil, paper, rubber, and combinations thereof. It may have a single or multi-layer construction. Suitable polymers for use as the backing member include, but are not limited to, polypropylene, polyethylene, polyester, ethylene vinyl acetate, ethylene vinyl alcohol, and combinations thereof Suitable natural wovens or non-wovens include non-toxic, water-soluble, digestible materials, such as carboxymethylcellulose.

The backing member is generally about less than 1 mm thick, preferably less than about 0.05 mm thick, and more preferably about 0.001 to 0.03 mm thick. It is generally less than about 20 mm wide, preferably less than about 15 mm wide, and most preferably less than about 10 mm wide. In addition to providing a substrate upon which the microstructures and binder are disposed, the backing also functions as a barrier that prevents saliva from washing the medicaments away from the target oral structure.

The term "microstructure," as used herein, means a feature having varying shapes and having dimensions of about 0.005 to 1.5 millimeter (about 0.0004 to 0.060 inch) in height, as measured from the surface from which the microstructures project. Each feature is typically separated from one another about 0.01 to 1 millimeter. Longer or shorter microstructures can be used and they may be separated at different distances, depending on factors such as the viscosity of the binder and medicaments, the nature of the treatment, and the oral structure being treated. The microstructures can be an ordered array, randomly placed or appear visually as a roughened surface. A roughened surface can be imparted to a substantially flat backing material through the use of a series of emboss rolls, where at least one of the rolls contains a pattern. Typically heat and/or pressure is used during the embossing step.

A preferred microstructure is illustrated in FIG. 2 where a stem having enlarged head (similar to a mushroom) projects outwardly from a first surface of the backing layer 20. Various manufacturing processes for forming the mushroom-like array are described in U.S. Pat. Nos. 4,290,174 (Kalleberg) and U.S. Pat. No. 4,984,339 (Provost et al.), WO 94/23610 and WO 98/30381, and PCT/US97/15960. An example of a suitable backing containing microstructures is a die-cut section of the hook side of a polypropylene microreplicated mechanical fastener, such as product number CD-200 diaper tape from Minnesota Mining and Manufacturing Company (3M), St. Paul, Minn.

The microstructures can have a variety of geometric shapes in cross section. For example, it can be rectangular, circular, semi-circular, triangular, square, hexagonal, and the like. The microstructures may also have a variety of shapes. For example, it can be cones, truncated cones, rods, pyramids, truncated pyramids, cubes, gumdrops, cylinders, nail heads, mushroom shaped members and the like.

In general, the number of microstructures per unit area is in the range of about 80 to 470 per square centimeter (about 500 to 3000 per square inch). An example of a suitable number is about 150 per square centimeter (about 900 per square inch). A higher or lower number of microstructures, however, may be optimal in certain circumstances. The optimal number may depend on factors such as the nature of the binder and medicaments.

The binder layer contains medicaments or active ingredients useful for treating the oral structures. The medicaments can be dispersed throughout the binder layer. Alternatively, it can be applied to one surface of the binder layer. In the latter case, carbamide peroxide, a useful medicament, can be supplied in powder form. After the binder layer is applied, e.g., coated, on to the backing containing microstructured surfaces, the carbamide peroxide can be applied, e.g., sprinkled or aerosolized, to the exposed surface of the binder. The medicament covers from about 10% to 90%, preferably from about 25% to 75% of the available binder layer surface area.

In one embodiment, the binder layer fills the vacancies between the microstructures and covers them, forming a film so that the binder becomes in contact with the oral structure when the inventive device is applied thereto. In this case, the binder layer has adhesive properties (e.g., tack) for it to bond to the target oral structures. In use, the inventive device is exposed to water, such as saliva, and the binder layer attaches to the structures under such conditions.

The tack of the binder layer can be assessed qualitatively by a "finger appeal" test involving a light touch and short contact time, and assigned a value of 1 through 5, where 1=tack free, 1.5=very low tack, 2=low tack, 2.5=low-to-medium tack, 3=medium tack, 3.5=medium-to-high tack, 4=high tack, and 5=very high tack. On this scale, SCOTCH MAGIC transparent tape from Minnesota Mining and Manufacturing Co. (3M), St. Paul, USA has a rating of 5. The binder layer has a tack of above 3, preferably above 4, using the foregoing scale. In one preferred embodiment, the binder layer shows little to no cohesive failure, i.e., little to no splitting of the binder, when subjected to the finger appeal test. In another preferred embodiment, the binder layer is an adhesive layer and not a gel.

In another embodiment, the binder layer fills at least a portion of the vacancies between the microstructures but does not necessarily cover them. In this case, the binder layer may or may not possess adhesive properties. A patterned adhesive can be used in combination with the binder. The patterned adhesive can be transferred from a carrier to, typically to the tips of, the microstructures. Useful patterned adhesives are disclosed in U.S. Pat. Nos. 5,344,681 (Calhoun et al.) and 5,449,540 (Calhoun et al.).

U.S. Pat. No. 5,344,681 discloses an adhesive transfer tape having a carrier with two opposite parallel surfaces. The first surface contains a series of recesses. Adhesive, preferably pressure sensitive adhesive, is disposed in the recesses to provide segments of the adhesive. An area substantially free of the adhesive surrounds the segments. In general, a method of making the patterned adhesive includes the following steps. A film web (e.g., polyethylene film of 0.1 mm thickness) is provided that has been coated (on both sides) with a release, such as a silicone (polysiloxane) based coating. Preferably the release level on the first side that comes into contact with the adhesive is different than that of the second side. The film is fed into a series of rollers to emboss the film creating shaped recesses (e.g., diamond shaped). One embodiment, disclosed in Example 4, has truncated four-sided pyramids, the recesses are about 0.13 mm deep, and the dimensions of the squares at the top and bottom are about 0.65 mm and 0.35 mm respectively. The recesses, containing a releasing agent, are then coated with a solution of adhesive, or more preferably, with a solventless curable adhesive. The adhesive is dried and/or cured. The adhesive, now in individual segments, can be transferred to the microstructures by a lamination step. Because of the release coating inside the recesses, the adhesive will readily transfer to the microstructures. It is not necessary that the segments of adhesive be in registration, i.e., match up with, all the microstructures. It is sufficient for the practice of this invention that a portion of the adhesive transfers. U.S. Pat. No. 5,344,681 discloses that a wide variety of coatable pressure sensitive adhesive can be used for the present invention, such as silicones, polyolefins, polyurethanes, polyesters, acrylics, rubber-resin and polyamides. Specific adhesives are disclosed in the U.S. Pat. No. 5,344,681 patent at column 6, lines 36 to 58.

The binder layer has a composition that is biocompatible with the user and has adhesive properties so as to allow for direct attachment to the desired oral structure. Most preferred are binder layers comprising acrylic acid, silicone based polyureas, acrylates, methacrylates, acrylamides, urethanes, and combinations thereof Particularly preferred is a binder layer comprising acrylic acid, acrylates, methacrylates, and combinations thereof The binder layer can be activated, i.e., release the medicaments, by a variety of mechanisms. Preferred mechanisms for activating the binder layer comprise light, heat, water, pressure, and combinations thereof More preferred mechanisms for activating the binder layer comprise water, pressure, and combinations thereof.

A particularly preferred adhesive useful as the binder layer is disclosed in U.S. patent application Ser. No. 09/367,455, which discloses a wet stick pressure sensitive adhesive (PSA). The PSA is nontoxic and has been tested for in vivo bioadhesion on the dried upper gingival tissues of dogs.

In a preferred embodiment, the wet stick PSA is coated directly to the flexible backing such that the PSA is in contact with the microstructure. The medicaments can then be applied to the exposed PSA surface. The PSA comprises the solventless polymerization product of: (a) about 30 to 70 parts by wt of (meth)acrylate ester monomer wherein the monomer, when homopolymerized, has a Tg of less than about 10° C. (conveniently labeled as component "A"); (b) about 70 to 30 parts by wt of hydrophilic acidic monomer (conveniently labeled as component "B"); and (c) about 10 to 100 parts based on 100 parts of the sum of components (a)+(b) of non-reactive plasticizing agent (conveniently labeled as component "C"). The PSA adheres to wet substrate surfaces. The term, "pressure-sensitive adhesive"

refers to a viscoelastic material that possesses the following properties: (1) aggressive and permanent tack, (2) adherence with no more than finger pressure, (3) sufficient ability to hold onto an substrate, and (4) sufficient cohesive strength to be removed cleanly from the substrate. "Wet-stick adhesive" refers to a material that exhibits PSA properties when adhered to a substrate that has been at least partially exposed to water. Wet-stick adhesives may or may not demonstrate pressure-sensitive adhesive properties under dry conditions. Also disclosed in the application are various methods for preparing the PSA.

Advantageously, all the methods used reduce, if not eliminate, the use of organic solvents or aqueous reaction media, such as water. Because many of the medicaments are water activated, solventless processing would allow for the addition of medicaments directly into the adhesive without having them activated prematurely. The processing, however, should not use conditions that would degrade the medicaments. One skilled in the art, knowing the stability of the medicaments, can pick processing conditions so as to preserve the medicaments' efficacy. The components used to prepare the wet stick adhesive are discussed below in detail.

For the "A" component, the wet-stick adhesives contain at least one monofunctional unsaturated monomer selected from the group consisting of (meth)acrylate esters of non-tertiary alkyl alcohols. The alkyl groups preferably have from about 4 to 12, more preferably about 4 to 8 carbon atoms. Preferred (meth)acrylate monomers have the following general Formula (I):

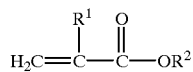

Formula (I)

wherein $R^1$ is H or $CH_3$, the latter corresponding to where the (meth)acrylate monomer is a methacrylate monomer. $R^2$ is broadly selected from linear or branched hydrocarbon groups and may contain one or more heteroatoms. The number of carbon atoms in the hydrocarbon group is preferably about 4 to 12, and more preferably about 4 to 8.

Examples of suitable (meth)acrylate monomers useful in the present invention include, but are not limited to, n-butyl acrylate, decyl acrylate, 2-ethylhexyl acrylate, hexyl acrylate, isoamyl acrylate, isodecyl acrylate, isononyl acrylate, isooctyl acrylate, lauryl acrylate, 2-methyl butyl acrylate, 4-methyl-2-pentyl acrylate, ethoxy ethoxyethyl acrylate, and mixtures thereof Particularly preferred are n-butyl acrylate, 2-ethylhexyl acrylate, isooctyl acrylate, lauryl acrylate, and mixtures thereof.

For the "B" component, the wet stick adhesives contain hydrophilic acidic comonomers that include, but are not limited to, those selected from ethylenically unsaturated carboxylic acids, ethylenically unsaturated sulfonic acids, ethylenically unsaturated phosphonic acids, and mixtures thereof Examples of such compounds include those selected from acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like, and mixtures thereof. Due to their availability and effectiveness in reinforcing (meth)acrylate pressure sensitive adhesives, particularly preferred hydrophilic acidic monomers are the ethylenically unsaturated carboxylic acids, most preferably acrylic acid.

Minor amounts of monomers copolymerizable with the (meth)acrylate monomers and hydrophilic acidic monomers can be used. Examples of such monomers include (meth) acrylamides, vinyl esters, and N-vinyl lactams.

The copolymerizable mixture comprises, based upon 100 parts by weight total, about 30 to 70, preferably 35 to 65, more preferably about 40 to 60 parts by weight of at least one (meth)acrylate monomer and about 70 to 30, preferably about 65 to 35, more preferably about 60 to 40 parts by weight of a hydrophilic acidic monomer.

The plasticizing agents (the "C" component) selected for use in the wet stick adhesive possess several properties. The (meth)acrylate monomers and hydrophilic acidic monomers are incompatible co-reactants and, without a solvent or aqueous reaction medium, fail to significantly interpolymerize. Thus, it is important that a compatible plasticizing agent be present during polymerization to serve as a polymerization medium for the co-reactants.

Because the plasticizing agent also modifies the rheology and transforms the copolymer into a material having wet-stick properties, the plasticizing agent should be compatible with the polymer. Any significant plasticizer bleeding or migration from the composition could result in loss of wet-stick adhesion properties.

Useful plasticizing agents, once mixed with the monomers, do not phase separate. By "phase separate," it is meant that by differential scanning calorimetry (DSC), no detectable thermal transition, such as a melting or glass transition temperature, can be found for the pure plasticizing agent in the wet stick adhesive. Some migration of the plasticizing agent from or throughout the wet stick adhesive can be tolerated, such as minor separation due to adhesive equilibrium or temperature influences, but the plasticizing agent does not migrate to the extent of phase separation between the wet stick composition and the plasticizing agent. Plasticizing agent compatibility with the wet stick adhesive can also be determined by the chemical nature of the plasticizing agent and the comonomers. For example, polymeric plasticizing agents based on polyether backbones (such as polyethylene glycols) are observed to be more compatible than polyester plasticizing agents, especially when higher levels of acidic comonomer, such as acrylic acid are used.

The plasticizing agent is non-volatile. The plasticizing agent should be present and stable under polymerization reaction to serve as a polymerization medium. To maintain wet-stick adhesion properties, the plasticizing agent should be present and not significantly evaporate from the polymerized wet-stick adhesive.

The plasticizing agent is non-reactive to prevent reaction or interference with the polymerization of the (meth)acrylate monomers and hydrophilic acidic monomers. Thus, plasticizing agents having acrylate functionality, methacrylate functionality, styrene functionality, or other ethylenically unsaturated free radically reactive functional groups are not used. Non-reactive plasticizing agents also reduce the inhibition or retardation of the polymerization reaction and/or the alteration of the final polymer structure that can occur if the plasticizing agent acts as a chain-transfer or chain-terminating agent. Such undesirable effects can adversely influence the performance and stability of the materials polymerized in the presence of these plasticizing agents. Chain termination can also result in undesirably high residual volatile materials (i.e., lower conversion of the comonomers).

Particularly useful plasticizing agents include polyalkylene oxides having weight average molecular weights of about 150 to 5,000, preferably of about 150 to 1,500, such as polyethylene oxides, polypropylene oxides, polyethylene glycols; alkyl or aryl functionalized polyalkylene oxides, such as PYCAL 94 (a phenyl ether of polyethylene oxide, commercially available from ICI Chemicals); benzoyl functionalized polyethers, such as Benzoflex 400 (polypropylene glycol dibenzoate, commercially available from Velsicol Chemicals) and monomethyl ethers of polyethylene oxides, and mixtures thereof.

The plasticizing agent can be used in amounts from about 10 to 100 pph, preferably about 30 to 100 pph (parts by weight per 100 parts of the (meth)acrylate monomers and hydrophilic acidic comonomers). The amount of plasticizer used depends upon the type and ratios of the (meth)acrylate monomers and hydrophilic acidic monomers used in the polymerizable mixture and the chemical class and molecular weight of the plasticizing agent used.

A free radical initiator is preferably added to aid in the polymerization of (meth)acrylate comonomers and acidic monomers. The type of initiator used depends on the polymerization process. Photoinitiators useful for polymerizing the monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1, 1-propanedione-2-(o-ethoxycarbonyl)oxime. An example of a commercially available photoinitiator is IRGACURE 651 (2,2-dimethoxy-1,2-diphenylethane-1-one, commercially available from Ciba-Geigy Corporation). Generally, the photoinitiator is present in an amount of about 0.005 to 1 weight percent, based on the weight of the polymerizable monomers. Examples of suitable thermal initiators include AIBN (2,2'-azobis(isobutyronitrile), hydroperoxides, such as tert-butyl hydroperoxide, and peroxides, such as benzoyl peroxide and cyclohexane peroxide.

Optionally, the reaction also includes the use of a chain transfer agent to control the molecular weight of the resulting adhesive. Suitable chain transfer agents include halogenated hydrocarbons such as carbon tetrabromide; sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether, and mixtures thereof.

The amount of chain transfer agent that is useful depends upon the desired molecular weight and the type of chain transfer agent. The chain transfer agent is typically used in amounts from about 0.001 part to 10, preferably about 0.01 to 0.5, more preferably about 0.02 to 0.20 parts by weight per 100 parts of total monomer.

One illustrative method for preparing the PSA involves the following acts: (a) combining a solventless polymerizable mixture comprising components A, B, and C; and (b) polymerizing the solventless polymerizable mixture to form a PSA that adheres to wet substrate surfaces.

Another method for preparing the PSA involves the following acts: (a) combining a solventless polymerizable mixture comprising components A, B, and C; (b) enveloping the solventless polymerizable mixture in a packaging material; and (c) exposing the enveloped polymerizable mixture to radiation sufficient to polymerize the solventless polymerizable mixture and to form a pressure sensitive adhesive that adheres to wet substrate surfaces.

Other solventless polymerization methods, such as the continuous free radical polymerization method described in U.S. Pat. Nos. 4,619,979 and 4,843,134; the essentially adiabatic polymerization methods using a batch reactor described in U.S. Pat. No. 5,637,646; and, the methods described for polymerizing packaged polymerizable mixtures described in U.S. Pat. No. 5,804,610 may be to prepare the wet stick adhesive. Detailed description of the various methods for preparing the wet stick adhesive an be found in U.S. patent application Ser. No. 09/367,455.

Yet another adhesive useful as a binder layer is disclosed is U.S. Pat. Nos. 5,670,557 (Dietz et al.) and U.S. Pat. No. 5,674,561. The patent discloses a polymerized microemulsion PSA having peel adhesion of at least 3 newtons/100 mm as measured according to PSTC-1 Test on a clean glass test plate. The PSA has a continuous phase of a hydrophobic PSA polymer and a continuous phase of a hydrophilic polymer. The adhesive is suitable for use in biomedical devices, skin coverings, and pharmaceutical delivery devices, among other applications. PSTC-1 is entitled "Peel Adhesion for Single Coated Tapes 180° Angle" and is available from the Pressure Sensitive Adhesive Tape Council of Chicago, Ill. Anhydrous formulations of this adhesive is preferred.

The medicaments contain an active compound or composition capable of causing a desired change to the oral structure. Exemplary desired changes include whitening, stain bleaching, stain removing, remineralizing to form fluorapatite, plaque removal, and tartar removal. Examples of suitable medicaments include, but are not limited to, hydrogen peroxide, carbamide peroxide, sodium fluoride, sodium monophosphate, pyrophosphate, chlorhexidine, polyphosphate, triclosan, enzymes, and combinations thereof Other useful medicaments include anti-inflammatory, antimicrobial, and other agents for treating soft tissue diseases, e.g., periodontitis treatment.

A common and useful dental bleaching agent contains about 10 wt. % to 16 wt. % carbamide peroxide (also referred to as urea hydrogen peroxide, urea peroxide, hydrogen peroxide carbamide, and perhydrol-urea). Also useful in this invention are over-the-counter compositions containing about 10% carbamide peroxide, available as GLY-OXIDE from Marion Laboratories, and PROXIGEL from Reed and Carnick.

The medicaments need to be compatible with the binder layer and the backing member. The medicament also needs to be stable in the binder during storage. In some embodiments, the medicament can be activated by water, e.g., saliva present in the user's mouth.

A user has several options available for applying the inventive device to the desired oral structure, all of which can be done without the use of a dental tray. In a preferred method, the device is supplied as substantially shown in FIG. 2. The user simply peels away the carrier 16 and applies the device directly to the desired oral structure 30 as shown in FIG. 3. The device remains on the oral structure for a period of time to receive desired effect, such as teeth bleaching. After the application period, the user simply removes what remains of device 12 and discards it.

In another method, a device 12 is supplied on carrier 16 without a binder. An adhesive layer (e.g., a double sided pressure sensitive tape) can be used to attach the two components until it is ready for use. Upon use, the user applies the binder containing medicaments, e.g., a paste containing bleaching solutions, on to the device 12, so that the paste is in direct contact with the microstructures. Under this approach, the paste should have adhesive properties. Useful pastes contain propylene glycol, glycerol, a thickener, such as carbapol, and a medicament or active ingredient, such as carbamide peroxide.

All references cited herein, whether patents or patent applications, are incorporated by reference, in their entirety.

The present invention may be suitably practiced in the absence of any element or item not specifically described in this document.

What is claimed is:

1. A device for delivering a medicament for treating oral structures, the device comprising:
   (a) a flexible backing having a substantially flat first surface having a plurality of microstructures protruding therefrom in a direction toward the oral structure to be treated; and
   (b) a binder layer having at least one medicament, said binder layer having an exposed surface area and disposed on at least a portion of said first surface and/or at least a portion of said microstructures,
   said device not containing a dental tray.

2. The device of claim 1, wherein said binder layer has pressure sensitive adhesive properties.

3. The device of claim 2, wherein said binder layer has a tack value higher than at least 3 according to the finger appeal test.

4. The device of claim 2, wherein said binder layer is a wet stick adhesive or a microemulsion adhesive.

5. The device of claim 4, wherein said wet stick adhesive comprises:
   (a) about 30 to 70 parts by weight (meth)acrylate ester monomer, wherein the monomer, when homopolymerized, has a Tg of less than about 10° C.;
   (b) about 70 to 30 parts by weight of hydrophilic acid monomer; and
   (c) about 10 to 100 parts, based on 100 parts of the sum of components (a)+(b), of non-reactive plasticizing agent.

6. The device of claim 4, wherein said at least one medicament is disposed on the exposed surface of said binder layer.

7. The device of claim 1, wherein said binder is selected from the group consisting of acrylic acid, silicone based polyureas, acrylates, methacrylates, acrylamides, urethanes, and combinations thereof.

8. The device of claim 1, wherein said flexible backing is selected from the group consisting of polymers, synthetic and natural wovens, synthetic and natural non-wovens, foil, paper, rubber, and combinations thereof.

9. The device of claim 8, wherein said polymer is selected from the group consisting of polyethylene, polyester, ethylene vinyl acetate, ethylene vinyl alcohol, and combinations thereof.

10. The device of claim 8, wherein said natural nonwoven is carboxymethylcellulose.

11. The device of claim 1, wherein said at least one medicament is selected from the group consisting of hydrogen peroxide, cabamide peroxide, sodium fluoride, sodium monophosphate, pyrophosphate, chlorhexidine, polyphosphate, triclosan, enzymes, anti-inflammatory, antimicrobial, and combinations thereof.

12. The device of claim 1 further comprising a carrier disposed on at least a portion of said binder layer and/or at least a portion of said microstructures.

13. The device of claim 1, wherein said microstructures are about 0.005 to 1.5 millimeter in height, measured from said first surface, and wherein said microstructures are separated from one another about 0.01 to 1 millimeter.

14. The device of claim 13, wherein said microstructures are integrally connected to said backing.

15. The device of claim 13, wherein said microstructures have an enlarged head resembling a mushroom.

16. A kit comprising the device of claim 1 and instructions for using said device.

17. The device of claim 1, wherein said microstructures provide obstacles that reduce the flow of said at least one medicament away from the oral structure to be treated.

18. A method of delivering a medicament for treating oral structures, said method comprising the following acts:
   (a) providing a dental device comprising:
      (i) a flexible backing having a substantially flat first surface, said first surface having a plurality of microstructures protruding therefrom in a direction toward the oral structure to be treated; and
      (ii) a binder layer comprising at least one medicament, said binder layer having an exposed surface and being disposed on at least a portion of said first surface of said backing and/or at least a portion of said microstructures,
   (b) applying said device to oral structures such that said binder is proximate to said oral structures.

19. The method of claim 18 wherein said binder layer is a wet stick adhesive comprising:
   (a) about 30 to 70 parts by weight (meth)acrylate ester monomer, wherein the monomer, when homopolymerized, has a Tg of less than about 10° C.;
   (b) about 70 to 30 parts by weight of hydrophilic acid monomer; and
   (c) about 10 to 100 parts, based on 100 parts of the sum of components (a)+(b), of non-reactive plasticizing agent;
   and said at least one medicament is disposed near the exposed surface of said binder layer.

20. The method of claim 18 wherein said microstructures provide obstacles that reduce the flow of said at least one medicament away from the oral structure to be treated.

* * * * *

UNITED STATES PATENT AND TRADEMARK OFFICE
CERTIFICATE OF CORRECTION

PATENT NO. : 6,435,873 B1
DATED : August 20, 2002
INVENTOR(S) : Burgio, Paul A.

It is certified that error appears in the above-identified patent and that said Letters Patent is hereby corrected as shown below:

<u>Column 10,</u>
Line 6, delete "an" and insert in place thereof -- can --.

Signed and Sealed this

Sixth Day of May, 2003

JAMES E. ROGAN
*Director of the United States Patent and Trademark Office*